United States Patent [19]

Humphrey et al.

[11] Patent Number: 5,668,157
[45] Date of Patent: Sep. 16, 1997

[54] CYANOGUANIDINES AS K-CHANNEL BLOCKERS

[75] Inventors: Stephen J. Humphrey; Kaushik D. Meisheri; James H. Ludens, all of Kalamazoo; Jackson B. Hester, Jr., Galesburg, all of Mich.

[73] Assignee: Pharmacia & Upjohn Company, Kalamzoo, Mich.

[21] Appl. No.: 666,502

[22] PCT Filed: Jan. 9, 1995

[86] PCT No.: PCT/US95/00024

§ 371 Date: Jun. 25, 1996

§ 102(e) Date: Jun. 25, 1996

[87] PCT Pub. No.: WO95/20579

PCT Pub. Date: Aug. 3, 1995

Related U.S. Application Data

[63] Continuation-in-part of Ser. No. 188,969, Jan. 8, 1994, abandoned.

[51] Int. Cl.$^6$ .......................... A61K 31/44; C07D 213/75
[52] U.S. Cl. ............................ 514/353; 546/306; 514/869
[58] Field of Search .................... 514/353, 869; 546/306

[56] References Cited

U.S. PATENT DOCUMENTS

| | | | |
|---|---|---|---|
| 4,057,636 | 11/1977 | Petersen | 424/263 |
| 5,006,523 | 4/1991 | Atwal | 514/227 |
| 5,401,758 | 3/1995 | Atwal et al. | 514/353 |
| 5,567,722 | 10/1996 | Humphrey et al. | 514/353 |

FOREIGN PATENT DOCUMENTS

| | | | |
|---|---|---|---|
| 92104287.5 | 9/1992 | European Pat. Off. | C07D 213/75 |
| 166119 | 1/1991 | Japan. | |
| 055209 | 12/1974 | United Kingdom. | |

| | | | |
|---|---|---|---|
| WO 94/04499 | 3/1994 | WIPO | C07D 213/75 |
| WO 94/04500 | 3/1994 | WIPO | C07D 213/75 |

OTHER PUBLICATIONS

G. Giebisch, Eur J Clin Pharmacol (1993) 44 [Suppl 1]:S3–S5, Diuretic action of potassium channel blockers.
Hans Jorgen Peterson, et al, Journal of Medicinal Chemistry, 1978, vol. 21, No. 8, pp. 773–781, Synthesis and Hypotensive Activity of N–Alkyl–n"–cyano–N'–pyridylguanidines.
J.K. Smallwood, et al., Pharm., 12:102–9 (1988).
D.W. Robertson, et al., Annual Reports in Medicinal Chemistry, 24, Ch 10, 91–100 (1989).

*Primary Examiner*—James H. Reamer
*Attorney, Agent, or Firm*—Donald L. Corneglio

[57] ABSTRACT

Cyanoguanidine compounds of formula (I) and its pharmaceutically acceptable acid addition salts wherein $R_1$ is hydrogen or methyl; $R_2$ is $C_1$–$C_6$alkyl, $C_2$–$C_6$alkenyl, $C_2$–$C_6$alkynyl, $C_3$–$C_5$cycloalkyl, $C_3$–$C_5$cycloalkenyl hydroxy methyl, methoxy-$C_1$–$C_5$alkyl, or $R_1$ and $R_2$ are combined to form a $C_3$–$C_6$carbocyclic ring; $R_3$ and $R_4$ are each independently selected to be hydrogen, $C_1$–$C_4$alkyl, F, Cl, Br, I or $CF_3$; $R_5$ is hydrogen, F or Cl; $R_6$ is hydrogen, —$NH_2$, —$NHCH_3$, —$NHC_2H_5$, —$NHCH(CH_3)_2$, —$N(CH_3)_2$, —$N(C_2H_5)_2$, $NH(CH_2)_m$, —$OC_1$–$C_3$alkyl (where m is 2 or 3), —$NHC(O)C_1$–$C_3$alkyl, Cl or Br; and n is 0 or 1. The compounds of formula (I) are potassium channel blockers useful in the treatment of cardiovascular disorders such as congestive heart failure and hypertension and as a diuretic.

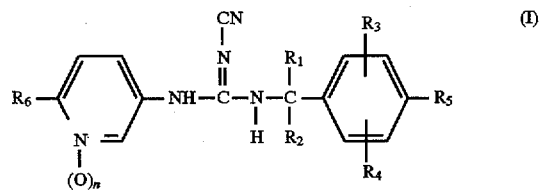

10 Claims, No Drawings

CYANOGUANIDINES AS K-CHANNEL BLOCKERS

This application is the national phase of international application PCT/US95/00024, filed 8 Jan. 1995, which was a continuation-in-part of U.S. Ser. No. 08/188,969, filed 8 Jan. 1994, now abandoned.

BACKGROUND OF THE INVENTION

The present invention is directed toward cyanoguanidine compounds which are potassium channel blockers useful in the treatment of cardiovascular disorders such as congestive heart failure and hypertension. The cyanoguanidine compounds of this invention, unlike other cyanoguanidines, block potassium channel conduction in vascular smooth muscle and in ATP-sensitive potassium channels in apical membranes of the kidney.

It is known that $K^+$ channels are important for regulating potassium excretion by the kidney and it has been proposed that inhibition of ATP-sensitive $K^+$ channel conduction in apical cell membranes of the thick ascending limb of Henle's loop would reduce potassium recycling across the membrane and thus reduce sodium resorption via the $Na^+$-$2Cl^-$-$K^+$ co-transporter. It has also been proposed that inhibition of the ATP-sensitive $K^+$ channels of apical membranes in principal cells of the initial and cortical collecting tubule would reduce $K^+$ secretion, the primary source of urinary potassium. $K^+$ channel antagonist activities necessary to produce the observed eukalemic natriuresis have been documented in the rat kidney.

The subject compounds are effective blockers for the ATP-sensitive potassium channels of the thick ascending limb of Henle's loop and the principal cells of the initial and cortical collecting tubules of the kidney. This activity results in an enhanced urinary excretion of sodium and water without enhanced potassium excretion. This provides a useful diuresis which is not complicated by an undesirable reduction in plasma potassium levels or hypokalemia.

Thus, the subject series of cyanoguanidines, although very closely related to the $K^+$ channel agonist pinacidil and related compounds, are potent $K^+$ channel antagonists.

INFORMATION DISCLOSURE STATEMENT

U.S. Pat. No. 4,057,636 discloses pyridylguanidine compounds structurally similar to the subject compounds except that the subject compounds have a multiply substituted pyridine ring and branched methylene linking group to a phenyl which can be optionally substituted. Surprisingly, the subject compounds are potassium channel blockers whereas the compounds of 4,057,636 are potassium channel openers.

Pinacidil, its pyridine N-oxide and its related pyridylcyanoguanidines are a class of compounds structurally related to the subject invention. Articles disclosing these compounds are as follows: Smallwood, J. K., J. Card. Pharm., 12:102–9 (1988); and Peterson, H. J., J. Med. Chem., 21(8):773–81 (1978).

Other publications include, JP 166119, published Jan. 2, 1991, discloses cyanoguanidine derivatives have a branched alkyl group at the C-1 position but no phenyl group attached thereto. GB 055209, Dec. 20, 1974, Leo Pharmaceutical, discloses N-cyano-N'-pyridyl guanidine as hypotensives.

European Patent Application 92104287.5 discloses compounds having a pyridine N-oxide and amine substitutions although not linked to a phenyl.

The state of the art on potassium channel mechanisms and pinacidil is discussed in Annual Reports in Medicinal Chemistry, Robertson D. W., et al. 24, Ch 10, 91–100 (1989).

SUMMARY OF THE INVENTION

In one aspect the present invention is a compound of Formula I and its pharmaceutically acceptable acid addition salts

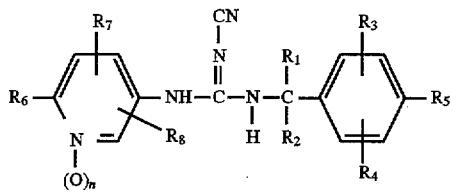

wherein $R_1$ is hydrogen or methyl;

$R_2$ is $C_1$–$C_6$alkyl, $C_2$–$C_6$alkenyl, $C_2$–$C_6$alkynyl, $C_3$–$C_5$cycloalkyl, $C_3$–$C_5$cycloalkenyl, hydroxymethyl, methoxy $C_1$–$C_5$alkyl, or $R_1$ and $R_2$ are combined to form a $C_3$–$C_6$carbocyclic ring;

$R_3$ and $R_4$ are each independently selected to be hydrogen, $C_1$–$C_4$alkyl, F, Cl, Br, I or $CF_3$;

$R_5$ is hydrogen, F or Cl.

$R_6$ is hydrogen, $NH_2$, $NHCH_3$, $NHC_2H_5$, $NHCH(CH_3)_2$, $N(CH_3)_2$, $N(C_2H_5)_2$, $NH(CH_2)_mOC_1$–$C_3$alkyl, NHC$(O)C_1$–$C_3$alkyl, F, Cl, Br, $C_1$–$C_3$alkyl, $NH(CH_2)_mF$, 1-imidazolyl, $NHOC_1$–$C_3$alkyl, NHOH, $NHSO_2C_1$–$C_3$alkyl, SH, $SC_1$–$C_3$alkyl, NHC(O)$OC_1$–$C_3$alkyl, NHC(O)NHC$_1$–$C_3$alkyl, $NHSO_2NHC_1$–$C_3$alkyl, $NHSO_2N(C_1$–$C_3$alkyl$)_2$ or amino acid amide;

$R_7$ is $C_1$–$C_7$alkyl, $NH_2$, $NHC_1$–$C_3$alkyl, $N(C_1$–$C_3$alkyl$)_2$, $CF_3$, F, Cl, Br, I, $OC_1$–$C_3$alkyl, OH, COOH, C(O)$OC_1$–$C_3$alkyl, C(O)$NH_2$, C(O)$NHC_1$–$C_3$alkyl, C(O)$C_1$–$C_3$alkyl, C(O)$N(C_1$–$C_3$alkyl$)_2$, $SO_2NH_2$, $SO_2NHC_1$–$C_3$alkyl, CN, $SO_2N(C_1$–$C_3$alkyl$)_2$, NHC(O)$C_1$–$C_3$alkyl, NHC(O)NHC$_1$–$C_3$alkyl, NHC(O)N(C$_1$–$C_3$alkyl$)_2$, $NHSO_2NHC_1$–$C_3$alkyl, $NHSO_2N(C_1$–$C_3$alkyl$)_2$, SH, $SC_1$–$C_3$alkyl, $NO_2$, $SO_2C_1$–$C_3$alkyl, NHC(O)$OC_1$–$C_3$alkyl, amino acid amide or hydrogen;

$R_8$ is hydrogen, $C_1$–$C_6$alkyl, $NH_2$, $NHC_1$–$C_3$alkyl, $N(CH_3)_2$, $N(C_2H_5)_2$, F, Cl, Br, $OC_1$–$C_3$alkyl or OH;

and where m is 2 or 3 and n is 0 or 1;

(except for those compounds where $R_8$ is hydrogen and $R_6$ is hydrogen, $NH_2$, $NHCH_3$, $NHC_2H_5$, $NHCH(CH_3)_2$, $N(CH_3)_2$, $N(C_2H_5)_2$, $NH(CH_2)_mOC_1$–$C_3$alkyl, NHC(O)$C_1$–$C_3$alkyl, Cl or Br).

In another aspect, the subject invention is useful as a potassium channel blocker and can be used in the treatment of cardiovascular disorders such as congestive heart failure, hypertension and shock.

DETAILED DESCRIPTION OF THE INVENTION

The present invention is directed toward compounds of Formula I and its pharmaceutically acceptable acid addition salts, as structurally depicted above. The compounds of Formula I include both enantiomers as well as salts and tautomeric forms.

It has been found that multiple substituents on the 3-pyridyl ring yield very good activity. At least one substituent must be present on the benzylic carbon and when only one alkyl substituent is present the activity resides with the (R) enantiomer. Particularly preferred are compounds with small cycloalkyl, alkyl or $R_1R_2$ carbocyclic substituents on the benzylic carbon and with a 3-chloro or 3-fluoro substituent on the phenyl ring.

Pharmaceutically acceptable acid addition salts of the Formula I, may be chosen from the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate.

The carbon content of various hydrocarbon-containing moieties is indicated by a prefix designating the minimum and maximum number of carbon atoms in the moiety, i.e., the prefix $C_i$-$C_j$ indicates a carbon atom's content of the integer "i" to the integer "j" carbon atoms, inclusive. For example, $C_1$-$C_3$alkyl refers to alkyl of 1-3 carbon atoms, inclusive, or methyl, ethyl, propyl, and isopropyl, and isomeric forms thereof.

$C_3$-$C_5$cycloalkyl is cyclopropane, cyclobutane, cyclopentane and isomeric forms thereof.

A "$C_3$-$C_6$ carbocyclic ring" means cyclopropyl, cyclobutyl, cyclopentyl, cyclohexyl, cyclobutenyl, cyclopentenyl or cyclohexenyl.

An "amino acid amide" is an amino acid attached to the pyridine ring by an amide linkage {—NHC(O)—} to an unsubstituted amino substituent.

Preferred compounds of Formula I are:

N-(5-Amino-6-chloro-3-pyridyl)-N"-cyano-N'-(1-phenylcyclobutyl)guanidine;

N-(6-Amino-2-methyl-3-pyridyl)-N"-cyano-N'-(1-phenylcyclobutyl)guanidine, methanol solvate; and N-(5-Amino-3-pyridyl)-N"-cyano-N'-(1-phenylcyclobutyl)guanidine.

The compounds of Formula I will thus be useful for treating cardiovascular disorders such as congestive heart failure and forms of hypertension that can benefit from a reduction in plasma fluid volume. In addition, the compounds of this invention, by virtue of their potassium channel blocking activity, will be useful for preventing the undesirable increase in plasma renin activity that might be expected to result from a reduction of plasma fluid volume or from reductions in blood pressure by other co-administered antihypertensive agents. This activity will enhance the antihypertensive activities of both agents.

This invention thus contemplates the co-administration of compounds of Formula I with other antihypertensive agents such as the ACE inhibitors, the β-adrenergic blockers, the $α_1$-adrenergic blockers, the $α_2$-adrenergic agonists, calcium channel blockers, and other vasodilators such as the nitrates and hydralazine, etc. In addition, the compounds of Formula I are useful for their antiarrhythmic activity and their ability to antagonize overdoses of potassium channel agonists, to prevent excessive hair growth, to increase insulin release, to treat shock, to control reflex hyperemia and to reduce body weight.

The enantiomers of the compounds of Formula I in which $R_1$ and $R_2$ are different are considered to be important variations of this invention. When $R_1$ is hydrogen and $R_2$ is alkyl the preferred enantiomer has the (R) absolute configuration. Also important are the pharmacologically acceptable acid addition salts, the pharmaceutical preparations for oral, transdermal and parenteral administration and the novel chemical intermediates and processes for the preparation of the compounds of Formula I.

The compounds can be administered intravenously, intramuscularly, topically, transdermally such as by skin patches, bucally, suppositorally or orally to man or other animals. The compositions of the present invention can be presented for administration to humans and animals in unit dosage forms, such as tablets, capsules, pills, powders, granules, sterile parenteral solutions or suspensions, oral solutions or suspensions, oil in water and water in oil emulsions containing suitable quantities of the compound, suppositories and in fluid suspensions or solutions.

For oral administration, either solid or fluid unit dosage forms can be prepared. For preparing solid compositions such as tablets, the compound can be mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The forms can be dissolved in an aqueous vehicle together with sugar, aromatic flavoring agents and preservatives to form a syrup. Suspensions can be prepared with an aqueous vehicle with the aid of a suspending agent such as acacia, tragacanth, methylcellulose and the like.

For parenteral administration, fluid unit dosage forms can be prepared utilizing the compound and a sterile vehicle. In preparing solutions the compound can be dissolved in the vehicle for injection and filter sterilized before filling into a suitable vial or ampoule and sealing. Adjuvants such as a local anesthetic, preservative and buffering agents can be dissolved in the vehicle. The composition can be frozen after filling into a vial and the water removed under vacuum. The dry lyophilized powder can then be sealed in the vial and reconstituted prior to use.

As diuretic agents the compounds of Formula I can be used in unit dosages of 1 to 1000 mg an oral or injectable preparations.

TABLE I

Physical and Analytical Data for the Cyanoguanidines of Formula I where $R_3$, $R_4$, and $R_5$ are hydrogen and n is zero.

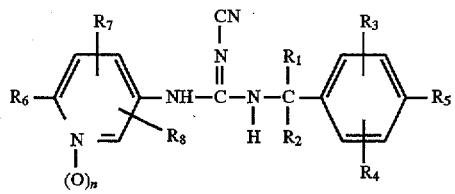

| Example # | $R^1$ | $R^2$ | $R^6$ | $R^7$ | $R^8$ | mp, °C. |
|---|---|---|---|---|---|---|
| 1 | $-CH_2-CH_2-CH_2-$ | | Cl | 5-$NH_2$ | H | 220–221 |
| 2 | $-CH_2-CH_2-CH_2-$ | | $NH_2$ | H | 2-$CH_3$ | 227–229 |
| 3 | $-CH_2-CH_2-CH_2-$ | | H | 5-$NH_2$ | H | 213–214 |
| 4 | $-CH_2-CH_2-CH_2-$ | | H | H | 2-$N(CH_3)_2$ | 204–205 |
| 5 | H | $CH_3{}^b$ | H | H | 2-$N(CH_3)_2$ | 111–128 |
| 6 | H | $C_2H_5{}^b$ | H | H | 2-Cl | 158–160 |
| 7 | $-CH_2-CH_2-CH_2$ | | $F-CH_2-CH_2-NH$ | H | H | 178.5–180 |
| 8 | H | $C_2H_5{}^b$ | $CH_3$ | H | H | 123–125 |
| 9 | H | $C_2H_5{}^b$ | H | 5-Br | H | c. |
| 10 | H | $C_2H_5{}^b$ | $F-CH_2-CH_2NH$ | H | H | 108–110 |
| 11 | H | $C_2H_5{}^b$ | H | H | 2-$CH_3$ | 134–135 |
| 12 | H | $C_2H_5{}^b$ | H | 5-$NH_2$ | H | 87–88 |
| 13 | $-CH_2-CH_2-CH_2-$ | | H | 5-$CH_3C(O)NH$ | H | 208–209 |
| 14 | H | $C_2H_5{}^b$ | $CH_3SO_2NH$ | H | H | 159.5–161.5 |

$^a$EtOAc solvate
$^b$(R) enantiomer
$^c$Amorphous solid (high resolution ms calculated for $C_{16}H_{16}BrN_5$; 357.0590; found 357.0595

Compounds of the subject invention were tested for diuretic effect as well as potassium channel blocking activity.

The results for potassium channel blocking were obtained by using isolated rabbit mesenteric artery (RMA) procedures. Norepinephrine (5 μM) was used to contract the RMA rings twice, with an hour separating the two contractions. During this hour the tissues equilibrated in physiological salt solution at a resting tension of 1 gram. Upon the plateau of the second contraction 1 μM pinacidil was added to all tissues and the resulting relaxation time course was studied for thirty minutes. Pinacidil at this concentration has been shown to produce maximal $K^+$ channel dependent vasodilation in the system. By studying the ability of the test compounds to inhibit this pinacidil-induced relaxation, the degree of potassium antagonism could be determined. The compounds were applied to the tissues for one hour between the two contractions and the pinacidil-induced relaxation was studied in the continuing presence of the compounds. Thus, the total time of pretreatment with the test compound was 75 minutes before the addition of pinacidil. Only one tissue was used per concentration of each compound, and in the case of no relaxation, the tissues were shown to be capable of relaxation by known vasodilators. The inhibitory effect of a compound was measured as percent inhibition of pinacidil relaxation at 15 minutes in comparison with the control.

Data for $K^+$ channel antagonist activity on rabbit mesenteric artery (RMA) and natriuretic efficacy after intraparenteral (IP) administration to rats are collected in Table II.

The diuretic activity was determined in female Harlan Sprague-Dawley rats weighing 200 to 230 grams that were fasted 15 hours overnight, and then were deprived of both food and water for an additional hour prior to dosing. Table II shows the measurement of net increase (above control) in urinary $Na^+$ excretion (μEq) for a 5 hour test period divided by the total of the three drug doses (mg/kg) administered IP in the diuretic screen. It approximates the area under the dose response curve. The vehicle was 20% dimethylacetamide (DMA; v/v) in a pH 7.4 phosphate buffer (0.58% $Na_2HPO_4$ and 0.13% $NaH_2PO_4.H_2O$). Sufficient drug was suspended in 1 to 2 ml of this vehicle to deliver doses of 5, 15 and 30 mg/kg in a volume of 0.5 ml (2–4 rats/dose). At least 2 vehicle control rats, and, for most tests, 2 standard diuretic treated rats were included in each experiment. Standards used as comparators included the $K^+$ retaining diuretic amiloride and the $K^+$ wasting diuretics furosemide, hydrochlorothiazide and metolazone.

Following their IP doses, the rats' urinary bladders were gently compressed to eliminate all pretreatment urine, and two identically treated rats were placed in a stainless steel metabolism cage equipped with a graduated test tube to collect voided urine. At 2 and 5 hours post treatment, the rats' bladders were again compressed, the volume of urine excreted by the pair of rats was recorded, and aliquots of urine were retained for analysis of $Na^+$ and $K^+$ concentrations with a NOVA-13 selective ion analyzer. Following the 5 hour urine collection, the rats were returned to their stock cages, and at least 1 week of recovery was allowed between a maximum of 3 diuretic tests.

The electrolyte concentrations detected in these urine samples were manually multiplied by their respective volumes to determine total milliequivalent (mEq) excretion of $Na^+$ and $K^+$ per pair of rats, and the results obtained with multiple racks per drug treatment were averaged. Increases in urinary $Na^+$ excretion of 50% or more above the pooled control tests were regarded as reflecting activity.

TABLE II

Natriuretic and Vascular Potassium Channel Antagonist Activities for the Compounds of TABLE II.

| Compound # | RMA K$^+$ Channel Antagonism % I (conc. μM)$^{a,b}$ | 5 h Net Natriuretic Efficacy (μEq Na$^+$/mg/kg)$^c$ |
|---|---|---|
| 1 | 90(0.1) | 39 |
| 2 | 96(0.3) | 77 |
| 3 | 93(0.3) | 50 |
| 4 | 87(2.0) | 10 |
| 5 | 17.4(5) | 15 |
| 6 | 77.5(0.1) | 48 |
| 7 | 24.3(1.0) | 60 |
| 8 | 84.1(10) | 25 |
| 9 | 94.6(10) | 12 |
| 10 | 72.3(10) | 34 |
| 11 | 91.6(10) | 25 |
| 12 | 85.8(10) | 26 |
| 13 | 6.4(10) | 15 |
| 14 | 2.3(30) | 21 |

Notes for TABLE II $^a$Lowest inhibitor concentration (μM) that gave greater than 20% inhibition or lowest concentration tested.
$^b$This is a measure of a compound's ability to inhibit the relaxation of norepinephrine (5 μM) contracted rabbit mesenteric artery rings by pinacidil (1 μM). It is expressed as percent inhibition. Compounds with 65% or greater inhibition at 5 μM are considered to be active, with 20–65% inhibition moderately active and with less than 20% inhibition inactive.
$^c$This represents the net increase (above control) in urinary Na$^+$ excretion (μEq) for the 5 hour test period divided by the total of the three drug doses (mg/kg) administered IP in the stage II diuretic screen in rats. It approximates the area under the dose response curve.

Table II shows that the compounds of the invention have good potassium channel antagonist activity as well as natriuretic activity.

PREPARATION OF INTERMEDIATES

Preparation 1

N-[6(2-Fluoroethylamino)-3-pyridyl]-N'-cyano-O-phenylisourea

Step 1: 2-(2-Fluoroethylamino)-5-nitropyridine

A stirred mixture of 2-chloro-5-nitropyridine (2.4 g, 0.015 mol), 2-fluoroethylamine hydrochloride (1.75 g, 0.0175 mol) and diisopropylethylamine (7.0 ml, 0.040 mol) in absolute ethanol (50 ml) was kept under nitrogen at ambient temperature (24° C.) for 22 hours, warmed slowly to the reflux temperature during 6 hours and refluxed for 18 hours. It was then concentrated in vacuo. The residue was mixed with saturated NaHCO$_3$ and extracted with EtOAc. The extract was washed with water and brine, dried (MgSO$_4$) and concentrated. The residue was chromatographed on silica gel with CH$_2$Cl$_2$. The product was crystallized from methyl tert butyl ether to give 1.25 g of the titled product, mp 126°–127° C.

Anal. calc'd for C$_7$H$_8$FN$_3$O$_2$; C, 45.41; H, 4.35; N, 22.70. Found: C, 45.41; H, 4.36; N, 22.84.

Step 2: 5-Amino-2-(2-fluoroethylamino)pyridine

A stirred mixture of the product from Step 1 (2.08 g, 0.0112 mol) and EtOH (25 ml), under nitrogen, was treated with stannous chloride dihydrate (12.6 g, 0.056 mol). The mixture was warmed at 75° C. for 30 minutes, cooled and mixed with ice water. This mixture was made alkaline (pH 8-9) with saturated NaHCO$_3$ and extracted with EtOAc. The extract was concentrated to give the titled product which was used without further purification in Step 3.

Step 3:

A stirred mixture of the product from Step 2 (0.0112 mol), diphenylcyanocarbonimidate (2.67 g, 0.0112 mol) and ethylene glycol dimethyl ether (25 ml) was kept under nitrogen for 18 hours at 24° C. The mixture was diluted with Et$_2$O (25 ml) and the solid was collected by filtration to give 1.04 g, mp 157°–158° C. of the titled product. The filtrate was purified by silica gel chromatography with 2.5% MeOH—CHCl$_3$ to give 0.39 g of additional product: MS m/z (relative intensity) 299 (M$^+$, 100), 278 (23.5), 266 (24.4), 206 (37.7), 184 (42.6), 172 (68.3), 94 (95.4).

Preparation 2

5-Amino-2-methanesulfonylamino-pyridine

Step 1: 2-[(Bismethanesulfonyl)amino]-5-nitropyridine

A stirred solution of 2-amino-5-nitropyridine (5.0 g, 35.9 mmol) in pyridine (200 ml), under nitrogen, was treated with 15.4 g (88.5 mmol) of methane-sulfonic anhydride and kept at 24° C. for 28.5 hours. It was then poured into ice water. The precipitate was collected by filtration, washed with water, dried and chromatographed on silica gel with 20% EtOAc-hexane. The product was crystallized from EtOAc to give 2.43 g of the titled product, mp 175°–177° C.

Anal. Calc'd for C$_7$H$_9$N$_3$O$_6$S$_2$: C, 28.47; H, 3.07; N, 14.23; S, 21.72. Found: C, 28.34; H, 2.93; N, 14.19; S, 21.67.

Step 2: 2-Methanesulfonylamino-5-nitropyridine

A stirred suspension of the product from Step 1 (2.43 g, 8.22 mmol) in MeOH (100 ml) was treated dropwise with 9.2 ml of IN NaOH and kept at 24° C. for 45 minutes. It was then filtered and the filtrate was concentrated to remove methanol. A solution of the residue in water (75 ml) was acidified (PH 2) with IN Hcl (8 ml). The precipitate was collected by filtration, washed with water, dried and recrystallized from MeOH to give 1.19 g of the titled product, mp 217°–219.5° C.

Anal. Calc'd for C$_6$H$_7$N$_2$O$_4$S: C, 33.18; H, 3.25; N, 19.35; S, 14.76. Found: C, 33.28; H, 3.33; N, 19.48; S, 14.60.

Step 3: 5-Amino-methanesulfonylamino-pyridine

A solution of the product from Step 2 (0.374 g, 1.72 mmol) in 95% EtOH (90 ml) was treated with 0.5 g of 10% palladium-on-carbon catalyst and hydrogenated at atmospheric pressure. The reaction was stopped when the theoretical amount of hydrogen had been consumed. The mixture was filtered through celite and the solid was extracted with warm (2:1) MeOH—CH$_2$Cl$_2$. The combined extracts and filtrate were concentrated and the residue was crystallized from MeOH to give 0.107 g of the titled product, mp 199°–202° C.

Anal. Calc'd for C$_6$H$_9$N$_3$O$_2$S: C, 38.49; H, 4.85; N, 22.44; S, 17.13. Found: C, 38.26; H, 4.79; N, 22.00; S, 16.52.

PREPARATION OF EXAMPLES

Example 1

N-(5-Amino-6-chloro-3-pyridyl)-N''-cyano-N'-(1-phenylcyclobutyl)guanidine

Step 1:
2-Chloro-3,5-diaminopyridine

A tablespoonful of Raney nickel catalyst in water was washed first with 95% EtOH and then with EtOAc; it was added to a solution of 2-chloro-3,5-dinitropyridine (4.00 g, 0.0196 mol) in EtOAc (150 ml) and the mixture was hydrogenated at an initial hydrogen pressure of 47.5 p.s.i. for 3 hours. The mixture was filtered through celite and the filtrate was concentrated. The residue was crystallized from CH$_2$Cl$_2$-pentane to give 1.83 g of the titled product.

Step 2: N-(5-Amino-6-chloro-3-pyridyl)-N'-cyano-O-phenylisourea

A stirred solution of the product from Step 1 (1.80 g, 0.0125 mol) in ethylene glycol dimethyl ether (DME, 50 ml)

was treated with diphenylcyanocarbonimidate (3.0 g, 0.0126 mol) and kept under nitrogen at ambient temperature (25° C.) for 96 hours. The precipitate was collected by filtration, washed with DME and dried to give 2.16 g of the titled product, mp 219°–220° C.

Step 3: N-(5-Amino-6-chloro-3-pyridyl)-N"-cyano-N'-(1-phenylcyclobutyl)guanidine A stirred mixture of the product from Step 2 (1.5 g, 0.0052 mol), 1-phenylcyclobutylamine (0.8 g, 0.00543 mol), N-methylmorpholine (1.37 ml, 0.0125 mol) and dioxane (30 ml) was refluxed, under nitrogen for 5 hours, cooled and filtered. The solid was washed with cold dioxane and $Et_2O$ and crystallized from acetonitrile to give 0.605 g of the titled product, mp 220°–221° C.

Anal. calc'd for $C_{17}H_{17}ClN_6$: C, 59.91; H, 5.03; Cl, 10.40; N, 24.66. Found: C, 59.57; H, 5.03; Cl, 10.34; N, 24.93.

Example 2

N-(6-Amino-2-methyl-3-pyridyl)-N"-cyano-N'-(1-phenylcyclobutyl)guanidine, methanol solvate Step 1: 2,5-Diamino-6-methylpyridine A mixture of 2-amino-5-nitro-6-methylpyridine (5.42 g, 0.0354 mol) (E. D. Parker and W. Shive, J. Amer. Chem. Soc., 69:63 (1947)), absolute EtOH (150 ml) and 10% palladium-on-carbon catalyst (0.488 g) was hydrogenated at an initial pressure of 40 p.s.i. for 18 hours. The catalyst was removed by filtration through celite and the filtrate was concentrated to give 4.34 g of the titled product.

Step 2: N-(6-Amino-2-methyl-3-pyridyl)-N'-cyano-O-phenylisourea

A stirred mixture of the product from Step 1 (4.34 g, 0.0353 mol), diphenylcyanocarbonimidate (8.4 g, 0.0353 mol) and ethylene glycol dimethyl ether (40 ml) was kept under nitrogen at ambient temperature (25° C.) for 18 hours. The mixture was concentrated and the residue was purified by silica gel chromatography and crystallization from MeOH-EtOAc-hexane to give 3.89 g of the titled product, mp 189°–190° C.

Anal. calc'd for $C_{14}H_{13}N_5O$: C, 62.91; H, 4.90; N, 26.20. Found: C, 63.20; H, 5.07; N, 25.30.

Step 3: N-(6-Amino-2-methyl-3-pyridyl)-N"-cyano-N'-(1-phenylcyclobutyl)guanidine, methanol solvate A stirred mixture of the product from Step 2 (2.00 g, 0.00748 mol), 1-phenylcyclobutylamine (1.13 g, 0.00823 mol), N-methylmorpholine (1.78 ml, 0.0162 mol) and dioxane (20 ml) was refluxed under nitrogen for 18 hours and concentrated in vacuo. The residue was chromatographed on silica gel with 3% MeOH-0.3% $NH_4OH$—$CHCl_3$ and the product thus obtained was crystallized from MeOH-EtOAc-hexane to give 1.8 g of the titled product, mp 227°–229° C.

Anal. calc'd for $C_{18}H_{20}N_6 \cdot 0.296$ $CH_4O$: C, 66.62; H, 6.47; N, 25.48; MeOH, 2.88. Found: C, 66.29; H, 6.47; N, 25.72; MeOH, 3.0.

Example 3

N-(5-Amino-3-pyridyl)-N"-cyano-N'-(1-phenylcyclobutyl)guanidine

Step 1: 3,5-Diaminopyridine

A mixture of 2-chloro-3,5-dinitropyridine (5.0 g, 0.0246 mol), methanol (150 ml) and 10% palladium-on-carbon catalyst (0.5 g) was hydrogenated at an initial hydrogen pressure of 50 p.s.i. The mixture was filtered through celite and the filtrate concentrated to give a mixture of 3,5-diaminopyridine and 2-chloro-3,5-diaminopyridine. A solution of this mixture in 2% aqueous NaOH (200 ml) and 2-propanol (100 ml) was treated, portionwise with 4 g of Raney aluminum-nickel alloy and stirred at ambient temperature (25° C.) for 90 minutes. It was then filtered through celite and the filtrate was concentrated in vacuo. The residue was extracted with hot EtOAc. The extract was dried ($Na_2SO_4$) and concentrated to give 2.05 g of the titled product.

Step 2: N-(5-Amino-3-pyridyl)-N'-cyano-O-phenylisourea

A stirred mixture of the product from Step 1 (2.05 g, 0.0188 mol) in ethylene glycol dimethyl ether (DME, 50 ml) was treated with diphenylcyanocarbonimidate (4.48 g, 0.0188 mol) and kept at ambient temperature (25° C.) for 18 hours. The precipitate was collected by filtration, washed with DME and dried to give 3.16 g of the titled product. The filtrate was concentrated in vacuo and the residue was chromatographed on silica gel with 5% MeOH—$CHCl_3$ to give 0.80 g of additional product, mp 179°–182° C.

Step 3: N-(5-Amino-3-pyridyl)-N"-cyano-N'-(1-phenylcyclobutyl)guanidine

A stirred mixture of the product from Step 2 (1.06 g, 0.00418 mol), 1-phenylcyclobutylamine (0.72 g, 0.0049 mol), N-methylmorpholine (1.15 ml, 0.0105 mol) and dioxane (22 ml) was refluxed, under nitrogen for 6 hours and kept at ambient temperature or 96 hours. The mixture was then diluted with $Et_2O$ and the solid was collected by filtration and chromatographed on silica gel with 5% MeOH-0.25% $NH_4OH$—$CHCl_3$. The resulting product was crystallized from acetonitrile to give 0.54 g of the titled product, mp 213°–214° C.

Anal. calc'd for $C_{17}H_{18}N_6$: C, 66.64; H, 5.92; N, 27.44. Found: C, 66.53; H, 5.92; N, 27.34.

Example 4

N-[2-(Dimethylamino)-3-pyridyl]-N"-cyano-N'-(1-phenylcyclobutyl)guanidine

Step 1: N'-Cyano-N-(2-dimethylamino-3-pyridyl)-O-phenylisourea

According to the procedure of Example 5, Step 3, 3-amino-2-dimethylaminopyridine (1.41 g, 0.0108 mol) was allowed to react with diphenylcyanocarbonimidate (2.45 g, 0.0108 mol) in ethylene glycol dimethyl ether (20 ml), under nitrogen for 18 hours. The reaction mixture was concentrated and the residue chromatographed on silica gel with mixtures of MeOH—$CHCl_3$ containing from 0 to 5% MeOH. The product amounted to 3.23 g.

Step 2: N-[2-(Dimethylamino)-3-pyridyl]-N"-cyano-N'-(1-phenylcyclobutyl)guanidine A stirred mixture of the product from Step 1 (3.23 g, 0.0115 mol), 1-phenylcyclobutylamine (1.73 g, 0.0126 mol) (A. Kalir and Z. Pelah, Israel J. Chem. 5:223 (1967)), N-methylmorpholine (2.74 ml, 0.0249 mol) and dioxane (40 ml) was refluxed, under nitrogen for 18 hours and concentrated in vacuo. The residue was mixed with EtOAc and concentrated to give a solid which was recrystallized from EtOAc-hexane to give 1.7 g, mp 204°–205° C. of the titled product.

Anal. calc'd for $C_{19}H_{22}N_6$: C, 68.24; H, 6.63; N, 25.13. Found: C, 67.91; H, 6.44; N, 24.94.

Example 5

(R)-N-[2-(Dimethylamino-3-pyridyl]-N"-cyano-N'-(1-phenylethyl)guanidine

Step 1: 2-(Dimethylamino)-3-nitropyridine

A stirred mixture of 2-chloro-3-nitropyridine (1.00 g, 0.00631 mol) in absolute EtOH (17 ml), under nitrogen, was treated, dropwise during 10 minutes, with 3.86 g (0.0214 mol) of 25% aqueous dimethylamine and kept at ambient temperature (25° C.) for 30 minutes. The mixture was mixed with water and extracted with EtOAc. The extract was washed with water, dried (MgSO$_4$) and concentrated to give 1.05 g of the titled product, a yellow oil.

Step 2: 3-Amino-2-dimethylaminopyridine

A stirred mixture of the product from Step 1 (1.05 g, 0.00628 mol), stannous chloride dihydrate (7.09 g, 0.03141 mol) and absolute EtOH (13.9 ml), under nitrogen, was warmed to 80° C. during 30 minutes and kept at that temperature for an additional 30 minutes. The mixture was cooled and kept at ambient temperature for 1 hour. It was then poured onto ice (200 ml), treated slowly with solid NaHCO$_3$ (2.88 g) and adjusted to pH 8 with saturated NaHCO$_3$. This mixture was extracted with EtOAc; the extract was washed with water, dried (Na$_2$SO$_4$) and concentrated to give the titled product (0.738 g), a dark oil.

Step 3: N'-Cyano-N-(2-dimethylamino-3-pyridyl)-O-phenylisourea

A stirred mixture of the product from Step 2 (0.738 g, 0.00538 mol), diphenylcyanocarbonimidate (1.28 g, 0.00538 mol) and ethylene glycol dimethyl ether (40 ml) was kept, under nitrogen, at ambient temperature (25° C.) for 7 hours. The mixture was concentrated and the residue was used in the next step without further purification.

Step 4: (R)-N-[2-(Dimethylamino)-3-pyridyl]-N''-cyano-N'-(1-phenylethyl)guanidine A stirred mixture of the crude product from Step 3, (R)-(+)-α-methylbenzylamine (1.01 ml, 0.00782 mol), N-methylmorpholine (1.69 ml, 0.0154 mol) and isopropanol (20 ml) was refluxed, under nitrogen for 5 hours and then concentrated. The residue was chromatographed on silica gel first with mixtures of MeOH—CHCl$_3$ containing from 1–10% MeOH to give an impure product which was rechromatographed on silica gel with mixtures of EtOAc-hexane containing from 1–50% EtOAc. The product obtained in this manner was dissolved in MeOH, decolorized with activated carbon and crystallized from MeOH-EtOAc-hexane to give 0.700 g of the titled product, mp 111°–128° C. (dec.).

Anal. Calc'd for C$_{17}$H$_{20}$N$_6$: C, 66.12; H, 6.54; N, 27.25. Found: C, 66.16; H, 6.52; N, 27.40.

The following Examples 6–14 were prepared using general procedures similar to those described in Examples 1–5 with the exception of various apparent starting materials. The preparation of new intermediates was described above prior to the Examples. The compounds of Examples 6–14 are named below and their structures depicted in Table I.

Example 6

(R)-N-(2-chloro-3-pyridyl)-N'-cyano-N''-(1-phenylpropyl)guanidine

Example 7

N-[6(2-Fluoroethylamino)-3-pyridyl]-N''-cyano-N'-(1-phenylcyclobutyl)guanidine

Example 8

(R)-N-(6-Methyl-3-pyridyl)-N''-cyano-N'-(1-phenylpropyl)guanidine

Example 9

(R)-N-(5-Bromo-3-pyridyl)-N''-cyano-N'-(1-phenylpropyl)guanidine

Example 10

(R)-N-[6-(2-Fluoroethylamino)-3-pyridyl]-N''-cyano-N'-(1-phenylpropyl)guanidine

Example 11

(R)-N-(2-Methyl-3-pyridyl)-N''-cyano-N'-(1-phenylpropyl)guanidine

Example 12

(R)-N-(5-Amino-3-pyridyl)-N''-cyano-N'-(1-phenylpropyl)guanidine

Example 13

N-(5-Acetylamino-3-pyridyl)-N''-cyano-N'-(1-phenylcyclobutyl)guanidine

A stirred solution of the product from Example 3 (0.87 g, 0.0028 mol) in pyridine (10 ml), was cooled under nitrogen in an ice bath and treated with acetyl chloride (0.22 ml, 0.0031 mol). The mixture was kept in the ice bath for 1 hour and at ambient temperature for 20 hours. It was then concentrated in vacuo. The residue was mixed with saturated NaHCO$_3$ and extracted with CHcl$_3$. The extract was concentrated in vacuo and the residue was chromatographed on silica gel with 5% MeOH-0.25% NH$_4$OH—CHcl$_3$. The product was crystallized from MeOH-EtOAc to give 0.343 g, mp 208°–209° C. and 0.0813 g, mp 207°–208° C. of the titled product.

Anal. Calc'd for C$_{19}$H$_{20}$N$_6$O: C, 65.50; H, 5.79; N, 24.12. Found: C, 65.31; H, 5.82; N, 24.18.

Example 14

(R)-N-(6-Methanesulfonylamino-3-pyridyl)-N''-cyano-N'-(1-phenylpropyl)guanidine

We claim:

1. A compound of Formula I and its pharmaceutically acceptable acid addition salts

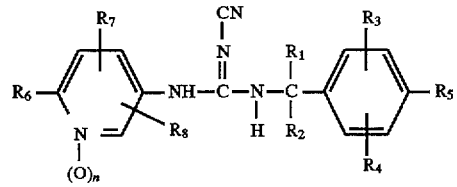

wherein

R$_1$ is hydrogen or methyl;

R$_2$ is C$_1$–C$_6$alkyl, C$_2$–C$_6$alkenyl, C$_2$–C$_6$alkynyl, C$_3$–C$_5$cycloalkyl, C$_3$–C$_5$cycloalkenyl, hydroxymethyl, methoxy C$_1$–C$_5$alkyl, or R$_1$ and R$_2$ are combined to form a C$_3$–C$_6$-carbocyclic ring;

R$_3$ and R$_4$ are each independently selected to be hydrogen, C$_1$–C$_4$alkyl, F, Cl, Br, I or CF$_3$;

R$_5$ is hydrogen, F or Cl;

R$_6$ is hydrogen, NH$_2$, NHCH$_3$, NHC$_2$H$_5$, NHCH(CH$_3$)$_2$, N(CH$_3$)$_2$, N(C$_2$H$_5$)$_2$, NH(CH$_2$)$_m$OC$_1$–C$_3$alkyl, NHC(O)C$_1$–C$_3$alkyl, F, Cl, Br, C$_1$–C$_3$alkyl, NH(CH$_2$)$_m$F, 1-imidazolyl, $NHOC_1-C_3$alkyl, NHOH, $NHSO_2C_1-C_3$alkyl, SH, $SC_1-C_3$alkyl, NHC(O)$OC_1-C_3$alkyl, $NHC(O)NHC_1-C_3$alkyl, $NHSO_2NHC_1-C_3$alkyl, $NHSO_2N(C_1-C_3alkyl)_2$ or amino acid amide;

$R_7$ is $C_1-C_7$alkyl, $NH_2$, $NHC_1-C_3$alkyl, $N(C_1-C_3alkyl)_2$, $CF_3$, F, Cl, Br, I, $OC_1-C_3$alkyl, OH, COOH, $C(O)OC_1-C_3$alkyl, $C(O)NH_2$, $C(O)NHC_1-C_3$alkyl, $C(O)C_1-C_3$alkyl, $C(O)N(C_1-C_3alkyl)_2$, $SO_2NH_2$, $SO_2NHC_1-C_3$alkyl, CN, $SO_2N(C_1-C_3alkyl)_2$, $NHC(O)C_1-C_3$alkyl, $NHC(O)NHC_1-C_3$alkyl, $NHC(O)N(C_1-C_3alkyl)_2$, $NHSO_2NHC_1-C_3$alkyl, $NHSO_2N(C_1-C_3alkyl)_2$, SH, $SC_1-C_3$alkyl, $NO_2$, $SO_2C_1-C_3$alkyl, $NHC(O)OC_1-C_3$alkyl, amino acid amide or hydrogen;

$R_8$ is hydrogen, $C_1-C_6$alkyl, $NH_2$, $NHC_1-C_3$alkyl, $N(CH_3)_2$, $N(C_2H_5)_2$, F, Cl, Br, $OC_1-C_3$alkyl or OH;

and where m is 2 or 3 and n is 0 or 1;

(except for those compounds where $R_8$ is hydrogen and $R_6$ is hydrogen, $NH_2$, $NHCH_3$, $NHC_2H_5$, $NHCH(CH_3)_2$, $N(CH_3)_2$, $N(C_2H_5)_2$, $NH(CH_2)_mOC_1-C_3$alkyl, $NHC(O)C_1-C_3$alkyl, Cl or Br).

2. The compound of claim 1 where $R_1$ and $R_2$ are joined to form cyclobutyl.

3. The compound of claim 1 where $R_1$ is hydrogen and $R_2$ is methyl or ethyl.

4. The compound of claim 1 where $R_6$ is $NH_2$, $NHCH_3$ or $NHC_2H_5$.

5. The compound of claim 1 where $R_7$ is $NH_2$.

6. The compound of claim 1 where $R_8$ is $CH_3$ or $N(CH_3)_2$.

7. The compound of claim 1 which is

N-(5-Amino-6-chloro-3-pyridyl)-N"-cyano-N'-(1-phenylcyclobutyl)guanidine;

N-(6-Amino-2-methyl-3-pyridyl)-N"-cyano-N'-(1-phenylcyclobutyl)guanidine, methanol solvate;

N-(5-Amino-3-pyridyl)-N"-cyano-N'-(1-phenylcyclobutyl)guanidine;

N-[2-(dimethylamino)-3-pyridyl]-N"-cyano-N'-(1-phenylcyclobutyl)guanidine;

(R)-N-[2-(Dimethylamino)-3-pyridyl]-N"-cyano-N'-(1-phenylethyl)guanidine;

(R)-N-(2-chloro-3-pyridyl)-N"-cyano-N'-(1-phenylpropyl)guanidine;

N-[6(2-Fluoroethylamino)-3-pyridyl]-N"-cyano-n'-(1-phenylcyclobutyl)guanidine;

(R)-N-(6-Methyl-3-pyridyl)-N"-cyano-N'-(1-phenylpropyl)guanidine;

(R)-N-(5-Bromo-3-pyridyl)-N"-cyano-N'-(1-phenylpropyl)guanidine;

(R)-N-[6-(2-Fluoroethylamino)-3-pyridyl]-N"-cyano-N'-(1-phenylpropyl)guanidine;

(R)-N-(2-Methyl-3-pyridyl)-N"-cyano-N'-(1-phenylpropyl)guanidine;

(R)-N-(5-Amino-3-pyridyl)-N"-cyano-N'-(1-phenylpropyl)guanidine;

N-(5-Acetylamino-3-pyridyl)-N"-cyano-N'-(1-phenylcyclobutyl)guanidine; or (R)-N-(6-Methanesulfonylamino-3-pyridyl)-N"-cyano-N'-(1-phenylpropyl)guanidine.

8. A method for blocking a potassium channel pathway in living tissue of animals and humans comprising administering a therapeutically effective amount of a compound of Formula I or a pharmaceutically acceptable acid addition salt thereof from claim 1.

9. The method of claim 8 wherein the compound of Formula I is administered intravenously, intramuscularly, topically, transdermally, bucally, suppositorally, orally, or parenterally.

10. The method of claim 8 where the compound is administered as a diuretic.

* * * * *